United States Patent
Plusquellic et al.

(10) Patent No.: US 8,642,982 B2
(45) Date of Patent: Feb. 4, 2014

(54) FAST SWITCHING ARBITRARY FREQUENCY LIGHT SOURCE FOR BROADBAND SPECTROSCOPIC APPLICATIONS

(71) Applicant: The United States of America, as represented by the Secretary of Commerce, NIST, Washington, DC (US)

(72) Inventors: David F. Plusquellic, Gaithersburg, MD (US); Kevin O. Douglass, Columbia, MD (US); Stephen E. Maxwell, Gaithersburg, MD (US); Joseph T. Hodges, Washington Grove, MD (US); David A. Long, Bethesda, MD (US); Gar-Wing Truong, Crawley (AU)

(73) Assignee: The United States of America, as represented by the Secretary of Commerce, NIST, Washington, DC (US)

( * ) Notice: Subject to any disclaimer, the term of this patent is extended or adjusted under 35 U.S.C. 154(b) by 0 days.

(21) Appl. No.: 13/827,476

(22) Filed: Mar. 14, 2013

(65) Prior Publication Data
US 2013/0228688 A1    Sep. 5, 2013

Related U.S. Application Data

(60) Provisional application No. 61/611,734, filed on Mar. 16, 2012, provisional application No. 61/722,812, filed on Nov. 6, 2012.

(51) Int. Cl.
*G01J 3/45* (2006.01)
*G01J 3/10* (2006.01)
*G01J 1/08* (2006.01)
*G01B 9/02* (2006.01)

(52) U.S. Cl.
USPC ... 250/493.1; 250/351; 359/332; 359/337.22; 359/237; 356/332; 356/73.1

(58) Field of Classification Search
USPC .......... 250/493.1, 351; 359/332, 337.22, 237; 356/332, 73.1
See application file for complete search history.

(56) References Cited

U.S. PATENT DOCUMENTS

| | | | | |
|---|---|---|---|---|
| 6,710,914 | B2* | 3/2004 | Arbore et al. | 359/330 |
| 7,103,402 | B2* | 9/2006 | Vo-Dinh | 600/476 |
| 7,889,348 | B2* | 2/2011 | Tearney et al. | 356/451 |

OTHER PUBLICATIONS

Chen, H. et al. High-accuracy continuous airborne measurements of greenhouse gases (CO2 and CH4) using the cavity ring-down spectroscopy (CRDS) technique, Atmos. Meas. Tech. 3, 375-386 (2010).

(Continued)

*Primary Examiner* — Nikita Wells
(74) *Attorney, Agent, or Firm* — Daphne L. Burton; Burton IP Law Group

(57) ABSTRACT

A fast switching arbitrary frequency light source for broadband spectroscopic applications. The light source may operate near 1.6 um based on sideband tuning using an electro-optic modulator driven by an arbitrary waveform generator. A Fabry-Perot filter cavity selects a single sideband of the light source. The finesse ($FSR/\Delta v_{FWHM}$) of the filter cavity may be chosen to enable rapid frequency switching at rates up to 5 MHz over a frequency range of 40 GHz (1.3 $cm^{-1}$). The bandwidth, speed and spectral purity are high enough for spectroscopic applications where rapid and discrete frequency scans are needed. Significant signal-to-noise advantages may be realized using the rapid and broadband scanning features of this system in many areas of spectroscopy, e.g., process monitoring and control, reaction dynamics, and remote sensing (e.g., greenhouse gas monitoring, biological/chemical agent screening).

24 Claims, 7 Drawing Sheets

(56) References Cited

OTHER PUBLICATIONS

Risby, T.H. & Solga, S.F. Current status of clinical breath analysis. Appl. Phys. B-Lasers Opt. 85, 421-26 (2006).

Hinkov, B et al., Time-resolved spectral characteristics of external-cavity quantum cascade lasers and their application to stand-off detection of explosives. Appl. Phys. B-Lasers Opt. 100, 253-260 (2010).

Keppler, F., Hamilton, J.T.G., Brass, M. & Rockmann, T. Methane emissions from terrestrial plants under aerobic conditions. Nature 439, 187-191 (2006).

Long, D.A. et al. Frequency-stabilized cavity ring-down spectroscopy. Chem. Phys. Lett. 536, 1-8 (2012).

Cygan, A. et al. High signal-to-noise-ratio laser technique for accurate measurements of spectral line parameters. Physical Review A 85 (2012).

Debecker, I., Mohamed, A.K. & Romanini, D., High-speed cavity ringdown spectroscopy with increased spectral resolution by simultaneous laser and cavity tuning. Opt. Express 13, 2906-2915 (2005).

He, Y. & Orr, B.J. Rapid measurement of cavity ringdown absorption spectra with a swept-frequency laser. Appl. Phys. B-Lasers Opt. 79, 941-945 (2004).

O'Keefe, A. & Deacon, D.A.G. Cavity ring-down optical spectrometer for absorption measurements using pulsed laser sources. Rev. Sci. Instrum. 59, 2544-2551 (1988).

Thorpe, M.J., Moll, K.D., Jones, R.J., Safdi, B. & Ye, J. Broadband cavity ringdown spectroscopy for sensitive and rapid molecular detection. Science 311, 1595-1599 (2006).

Del'Haye, P., Arcizet, O., Gorodetsky, M.L., Holzwarth, R. & Kippenberg, T.J. Frequency comb assisted diode laser spectroscopy for measurement of microcavity dispersion. Nat. Photonics 3, 529-533 (2009).

Bernhardt, B. et al. Cavity-enhanced dual-comb spectroscopy. Nat. Photonics 4, 55-57 (2010).

Galatry, L. Simultaneous effect of Doppler and foreign gas broadening on spectral lines. Physical Review 122, 1218-1223 (1961).

Miller, C.E. & Brown, L.R. Near infrared spectroscopy of carbon dioxide I.(OCO)-O-16-C-12-O-16 line positions. J. Mol. Spectrosc. 228, 329-354 (2004).

Hodges, J.T., Layer, H.P., Miller, W.W. & Scace, G.E. Frequency-stabilized single-mode cavity ring-down apparatus for high-resolution absorption spectroscopy. Rev. Sci. Instrum. 75, 849-863 (2004).

* cited by examiner

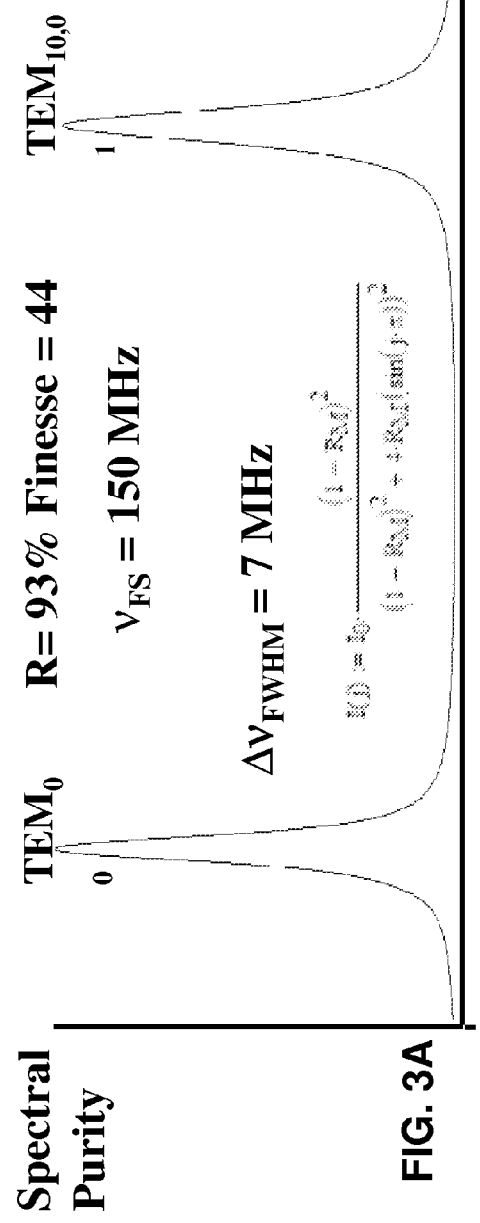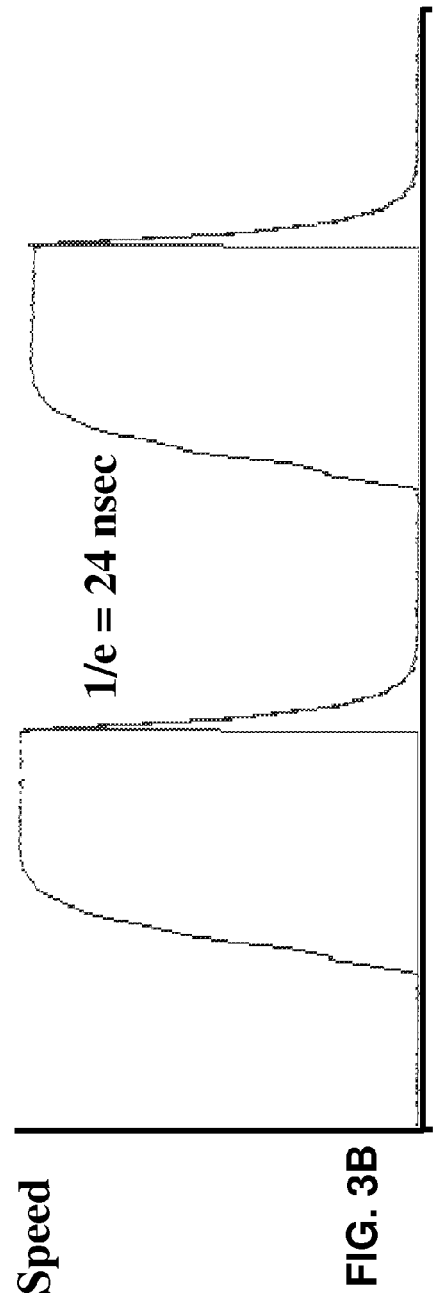
FIG. 3A
FIG. 3B

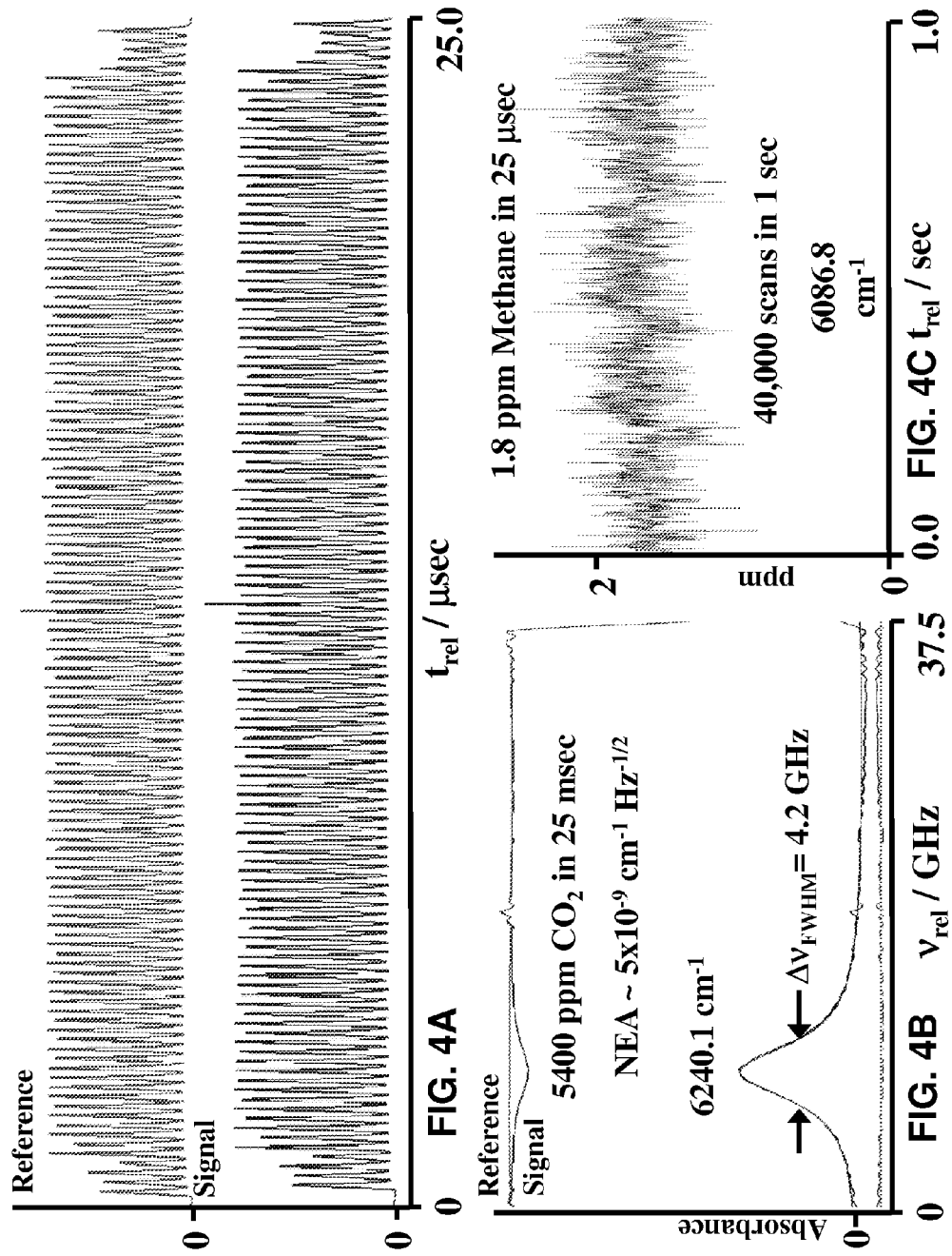

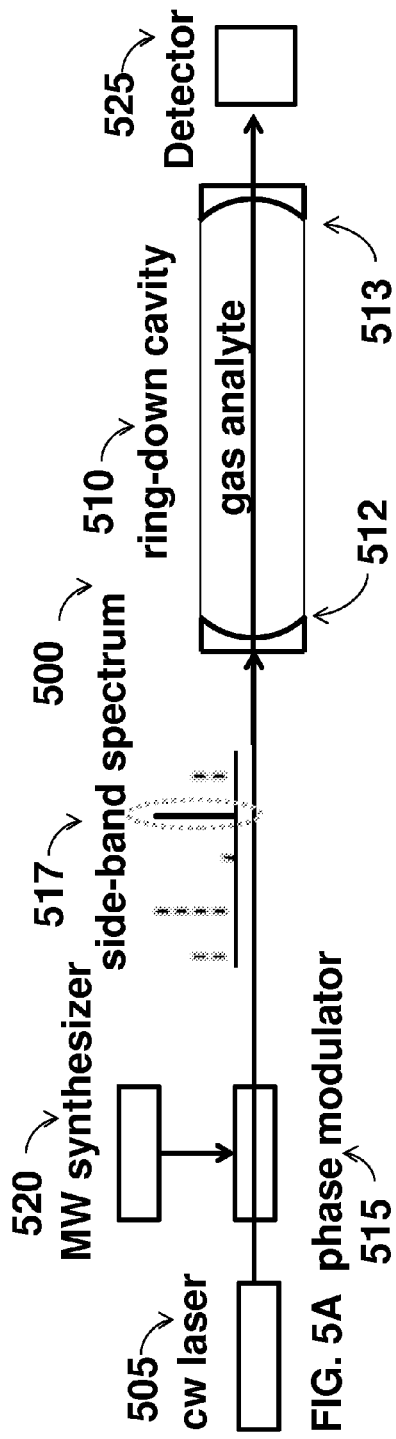
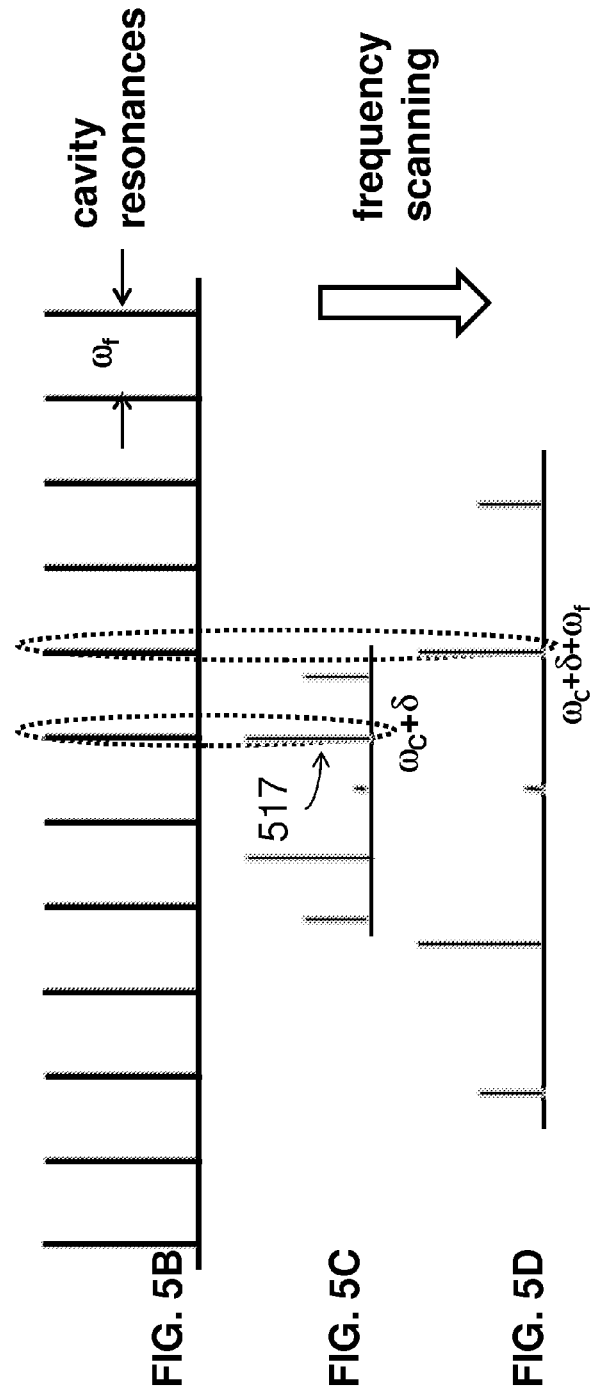

FAST SWITCHING ARBITRARY FREQUENCY LIGHT SOURCE FOR BROADBAND SPECTROSCOPIC APPLICATIONS

CROSS-REFERENCE TO RELATED APPLICATIONS

The present application claims priority to provisional application Ser. No. 61/611,734, filed on or about Mar. 16, 2012, entitled "A Fast Switching Arbitrary Frequency Light Source for Broadband Spectroscopic Applications", naming David Plusquellic, Kevin O. Douglass and Stephen E. Maxwell. The present application also claims priority to provisional application Ser. No. 61/722,812, filed on or about Nov. 6, 2012, naming inventors David F. Plusquellic, Kevin O. Douglass, Stephen E. Maxwell, Joseph T. Hodges and David A. Long. The contents of these provisional applications are incorporated by reference, the same as if fully set forth.

STATEMENT REGARDING FEDERALLY SPONSORED RESEARCH/DEVELOPMENT

The subject matter of this patent application was invented by employees of the United States Government. Accordingly, the United States Government may manufacture and use the invention for governmental purposes without the payment of any royalties.

BACKGROUND OF THE INVENTION

1. Field of Invention

The present disclosure relates to light sources and, more particularly, to a fast switching arbitrary frequency light source for broadband spectroscopic applications.

2. Description of Related Art

Differential Absorption Light Detection and Ranging (DIAL) is a laser based method that may be used to measure and map concentrations and emissions of molecules in the atmosphere. The DIAL method may be performed by slow-switching lasers from a single on-resonance frequency to a single off-resonance frequency of the line of interest in the atmosphere.

The DIAL method is subject to drawbacks. For example, this method may be subject to retrieval errors in concentration because of the small number of spectral intervals measured across the line. This method may also be subject to retrieval errors because of changes in the atmosphere that may occur between the on- and off-resonance measurements.

There is a need for a laser-based method or device that enables retrieval of multiple points across the pressure broadened line of interest and that permits operation over time intervals much shorter than changes in the atmospheric conditions.

In order to perform cavity-enhanced or cavity ring-down measurements, some prior art methods and devices acquire lock of the light source to a mode of the cavity. These prior art methods and devices then perform signal averaging at that frequency, step the laser frequency and then reacquire lock for the next set of measurements.

However, these prior art methods and devices suffer from drawbacks in that it is difficult to maintain a single mode of operation of the laser during tuning. Also, a long period of time may be needed to reacquire a lock of the light source, and there is a lack of immunity to low frequency noise over the period of time needed to scan over the full line.

There is a need for a laser-based method or device that facilitates maintaining a single mode operation of the laser during tuning.

There is also a need for a laser-based method or device that overcomes difficulties associated with the time needed to reacquire lock of the light source. There is a need for a laser-based method that overcomes difficulties associated with lack of immunity to low frequency noise over the long period of time needed to scan over the full line.

BRIEF SUMMARY OF DISCLOSURE

The present disclosure addresses the needs described above by providing a laser-based method that enables retrieval of a relatively large number of spectral intervals measured across the pressure broadened line of interest. The present method also permits operation over time intervals much shorter than changes in atmospheric conditions. The present method further permits a single cavity enhanced or ring-down measurement at each cavity mode across the full line shape in the shortest time possible without ever tuning the laser. Since the full line is observed after each scan, signal averaging may be performed by repeating the scan sequence until the desired signal-to-noise ratio is achieved.

In accordance with one embodiment of the present disclosure, a fast switching arbitrary frequency light source for broadband spectroscopic applications is provided. The light source comprises a waveguide-based electro-optic modulator and a tunable microwave source configured to drive the electro-optic modulator. The tunable microwave source has a speed substantially commensurate with the measurement speed of the waveguide-based electro-optic modulator. The light source also comprises a selection device configured to select a single frequency component from multiple discrete frequencies of light received from the electro-optic modulator; and a laser device configured to stabilize the laser device to the selection device.

In accordance with another embodiment of the present disclosure, a fast switching arbitrary frequency light source for broadband spectroscopic applications is provided. The light source comprises a waveguide-based electro-optic modulator, and a tunable microwave source configured to drive the electro-optic modulator. The tunable microwave source has a speed substantially commensurate with the measurement speed of the waveguide-based electro-optic modulator.

The light source further includes a filter cavity defined by at least two mirrors, the filter cavity being configured to select a single frequency component from multiple discrete frequencies of the electro-optic modulator. The filter cavity further includes an absorbing medium in an optical path between the at least two mirrors.

The light source still further includes a laser device configured to provide a frequency offset that stabilizes the laser device relative to the filter cavity, and a beam splitter configured to sample at least a portion of the output from the laser device and to use that sampled portion to stabilize the laser device relative to the filter cavity. The light source yet further includes a detection sensitivity improvement device configured to improve detection sensitivity by increasing the total optical path length through a sample volume; and a cavity enhancement device configured to select a single sideband of the electro-optic modulator, said sideband being resonant with optical cavity modes of the cavity enhancement device.

In accordance with yet another embodiment of the present disclosure, a method is disclosed for providing a fast switching arbitrary frequency light source. The method comprises providing a waveguide-based electro-optic modulator, a tunable microwave source, a laser device and a selection device. The method further comprises driving the electro-optic modulator with the tunable microwave source; selecting a single frequency component from multiple discrete frequencies received from the electro-optic modulator; and stabilizing the laser device relative to the selection device, including by providing a frequency offset that stabilizes the laser device relative to the selection device.

These, as well as other objects, features and benefits will now become clear from a review of the following detailed description of illustrative embodiments and the accompanying drawings.

BRIEF DESCRIPTION OF DRAWINGS

FIGS. 3A and 3B are graphical illustrations of the measured transmission of one implementation of the filter cavity (top panel) of the scan leg (without sidebands) and the temporal response of the filter cavity when the electro-optic modulator (EOM) is driven with square pulses from the arbitrary waveform generator (AWG), in accordance with one embodiment of the present disclosure.

FIGS. 4A, 4B and 4C are graphical illustrations of the measured absorption signals of two different gases contained in a multi-pass cell and at atmospheric pressure in accordance with one embodiment of the present disclosure.

FIGS. 5A-5D are representations of a cavity-enhanced spectrometer which utilizes the fast switching arbitrary frequency light source with the gas analyte placed within the filter cavity.

DETAILED DESCRIPTION OF THE DISCLOSURE

The present disclosure describes a fast switching, arbitrary frequency light source for broadband spectroscopic applications. The light source of the present disclosure may operate near 1.6 micrometer in wavelength (μm) based on single sideband tuning using an electro-optic modulator (EOM) or acousto-optic modulator (AOM) or may operate at any frequency where modulators are available. The electro-optic modulator may be driven by an arbitrary waveform generator (AWG). A Fabry-Perot filter cavity may be used to transmit a single sideband and block the carrier and other sidebands of the modulated light source.

The finesse of filter cavity may be chosen to enable rapid frequency switching at rates well in excess of 1 Megahertz (MHz) over a frequency range only limited by bandwidths of the AWG and EOM. For purposes of the present disclosure, finesse may be defined as the ratio of the free spectral range to the full width of the transmission peaks at half maximum for the filter cavity, or other resonator. Extending the frequency coverage is possible using either the higher order modes of the EOM or higher bandwidth modulators (currently available to ±40 GHz). Generation of higher frequencies using arbitrary waveform generators may be possible using amplifier/multiplier chains equal to or greater than 2 THz (66 cm$^{-1}$). The bandwidth, speed and spectral purity of the current system are high enough for many spectroscopic applications where rapid and discrete frequency scans are needed.

A number of spectroscopic applications or measurement techniques may be implemented using the light sources and methods disclosed herein. For example, one spectroscopic application is the measurement of the full direct absorption profile in a sample cell. Another possible spectroscopic application is the measurement of cavity-enhanced or cavity ringdown signals over a path length. A third possible spectroscopic application is measurement of the hard target absorption spectrum over a particular path length in the atmosphere. Using the light sources and method described herein, these measurements may be performed at the maximum possible scan speed. The combination of frequency and amplitude accuracy and precision with which these measurements may be obtained using the present light source is unparalleled.

Figure 1:
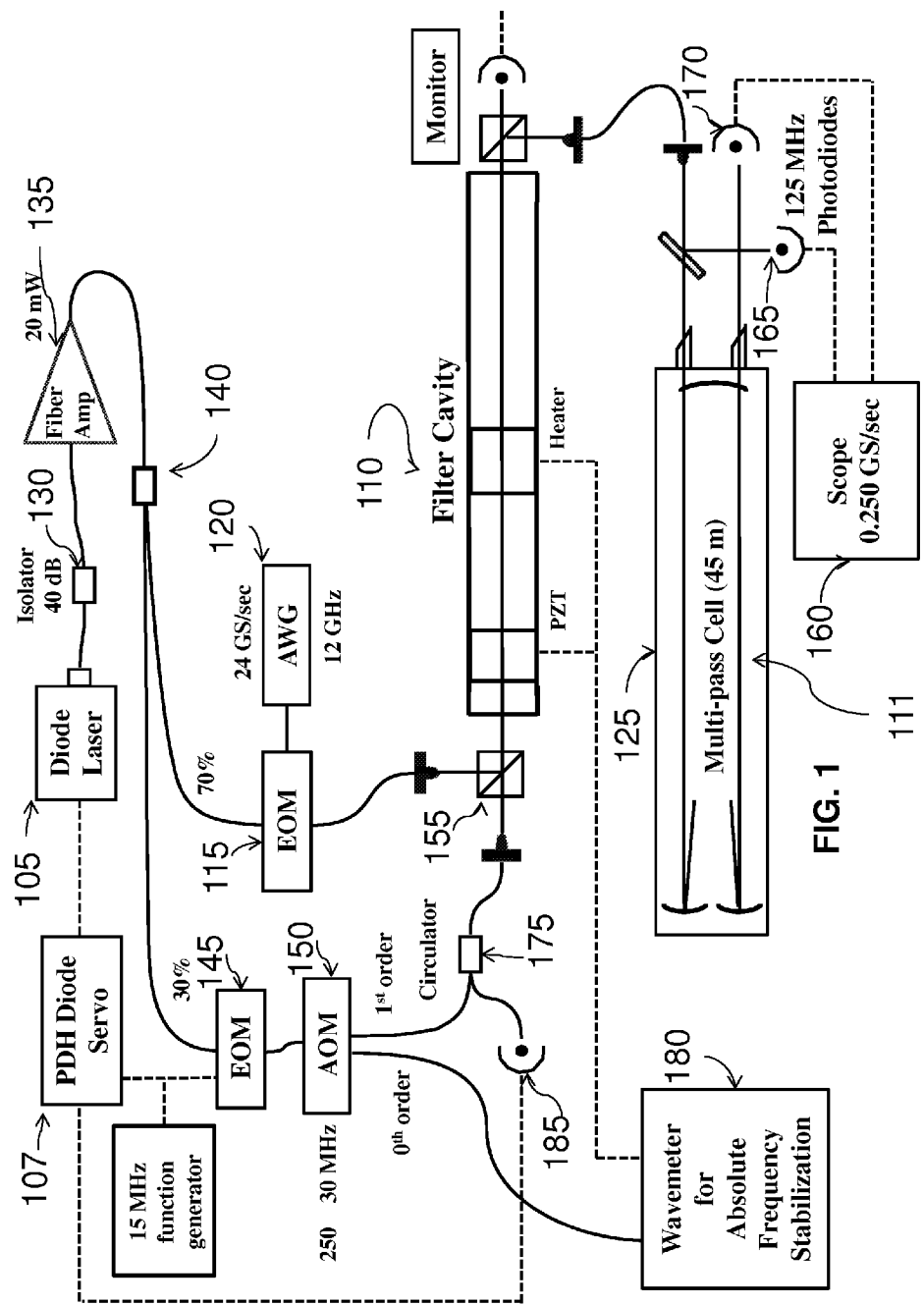
FIG. 1 is a diagram of a fast switching arbitrary frequency light source in accordance with one embodiment of the present disclosure.

Referring now to FIG. 1 illustrated is a fast switching arbitrary frequency light source in accordance with one embodiment of the present disclosure. Components of the fast switching arbitrary frequency light source 100 may include a laser device 105, a selection device 110 that provides for single sideband selection, and a waveguide based electro-optic modulator (EOM) 115 that is driven by a tunable microwave source 120.

In the embodiment shown in FIG. 1, the laser device 105 is an external cavity single frequency diode laser. However, in lieu of an external cavity single frequency diode laser, the laser device 105 may be any single frequency laser source that can transmit through a modulator and/or any type of laser that provides any method for stabilization relative to the selection device 110. Alternatives to the external cavity diode laser include but not limited to ring lasers, monolithic semiconductor lasers and fiber lasers.

In the present embodiment, the tunable microwave source 120 is an arbitrary waveform generator AWG having 12 GHz of bandwidth. However, the microwave source 120 may be any tunable microwave source having a speed commensurate with or exceeding the maximum speed of the measurement technique or electro-optic modulator 115 or other sideband generating device, whichever is slower. For purposes of the present disclosure, the maximum speed of the measurement technique is defined as the minimum time required to switch between different frequencies with sufficient power to make the measurement, as described in more detail hereinbelow.

In the present embodiment, the selection device 110 is a medium finesse Fabry-Perot confocal filter cavity which may or may not have an absorbing medium disposed between mirrors disposed at the end of the filter cavity. However, other devices may be used in lieu of the Fabry Perot filter cavity for single sideband selection or to generate a microwave tunable frequency light source. For example, in-phase quadrature (I/Q) modulators and/or a Mach-Zehnder interferometer and/or other optical filter devices may be used in lieu of the filter cavity.

In the present illustration, the detection sensitivity improvement device 125 is a multi-pass cell with a path length of 45 meters. However, it should be understood that other devices may be used for detection sensitivity improvement. For example, in lieu of multipass cell 125, any representation may be used of a absorption pass where a sample may be introduced.

The laser device 105 may be fiber-coupled through an optical isolator 130, and then amplified to about twenty milliwatts (20 mW) using a booster amplifier 135. The output from the amplifier 135 may be split into two legs using a 70/30 fiber splitter 140. A seventy percent (70%) leg may be used for high speed scanning, and a thirty percent (30%) leg used for stabilization of the diode laser and filter cavity. The 70% leg is sometimes referred to hereinafter as the scan leg, while the 30% leg is sometimes referred to hereinafter as the lock leg. In lieu of a fiber splitter, another method for beam sampling the output of the laser may be used, e.g., a beam sampling mirror.

The 30% leg may be fiber-coupled to a waveguide-based electro-optic modulator 145 to add fifteen (15) MHz sidebands for use in the stabilization loops discussed herein. The output from EOM 145 may be fiber coupled to an acousto-optic modulator (AOM) 150. The AOM 150 may be driven near its center frequency of two hundred fifty (250) Megahertz to generate a tunable sideband using a radio frequency source. This radio frequency source may be frequency-referenced to a ten (10) MHz Rubidium source or other frequency standard source.

The sideband of the AOM may be tunable over ±thirty (30) MHz with greater than five percent (5%) efficiency. The first-order sideband may also be fiber coupled to a three port optical circulator 175. The output from the AOM 150 may be free space propagated through a polarizing beam splitter (PBS) 155 and then off-axis coupled to the filter cavity 110.

The signal from a twenty (20) MHz bandwidth photodiode 185 may monitor the reflected beam from the circulator 175. This photodiode signal may be mixed in the diode servo 107 with the 15 MHz reference and demodulated to produce a Pound-Drever-Hall (PDH) error signal. Alternatively to producing a PDH error signal, any frequency (FM) or amplitude modulation (AM) technique, may be used for generation of error signal. The error signal may be conditioned in a 10 MHz passband proportional/integral (PI) gain controller.

The output from the gain controller may provide closed-loop feedback control to the current of diode laser 105 for stabilization to the filter cavity 110, made possible using diode servo 107. The lock stability of the laser may be less than a kilohertz (1 kHz). Other means may be provided to stabilize the filter selection device to an absolute frequency standard such as a wavemeter or optical frequency comb as shown collectively as 180.

The seventy percent (70%) leg of the output from fiber splitter 140 may be fiber coupled to a second waveguide-based EOM 115 driven by an arbitrary waveform generator 120. The two channels of the arbitrary waveform generator 120 may be interleaved to give a twenty-four gigasamples per second (24 GS/sec) clock rate having near twelve Gigahertz (12 GHz) of bandwidth. The arbitrary waveform generator 120 may have a maximum waveform output of 0.7 $V_{pp}$. It may be desirable to drive the EOM 115 with up to or more than a three (3) radian phase shift where the second-order sideband has maximum amplitude. To achieve this condition, the microwave source 120 may be amplified by twenty-four decibels (24 dB) in a (0.1-12) GHz amplifier. The EOM output may be free space propagated through the polarizing beam splitter and mode matched to the filter cavity.

To improve the portability of the system and output beam quality, the transmitted sideband may be coupled back into a single mode fiber and then launched for free space coupling to the multi-pass cell 125. Prior to the multi-pass cell 125, a five percent (5%) portion may be sampled for normalization purposes. The overall throughput efficiency of the filter cavity 110 may be in excess of ten percent (10%) of total input power. A fast digital oscilloscope 160 and matched indium gallium arsenide (InGaAs) photodiodes 165, 170 operating at 125 MHz may be used to simultaneously measure the absorption signal and reference power at each frequency step of the AWG 120.

Figure 2:
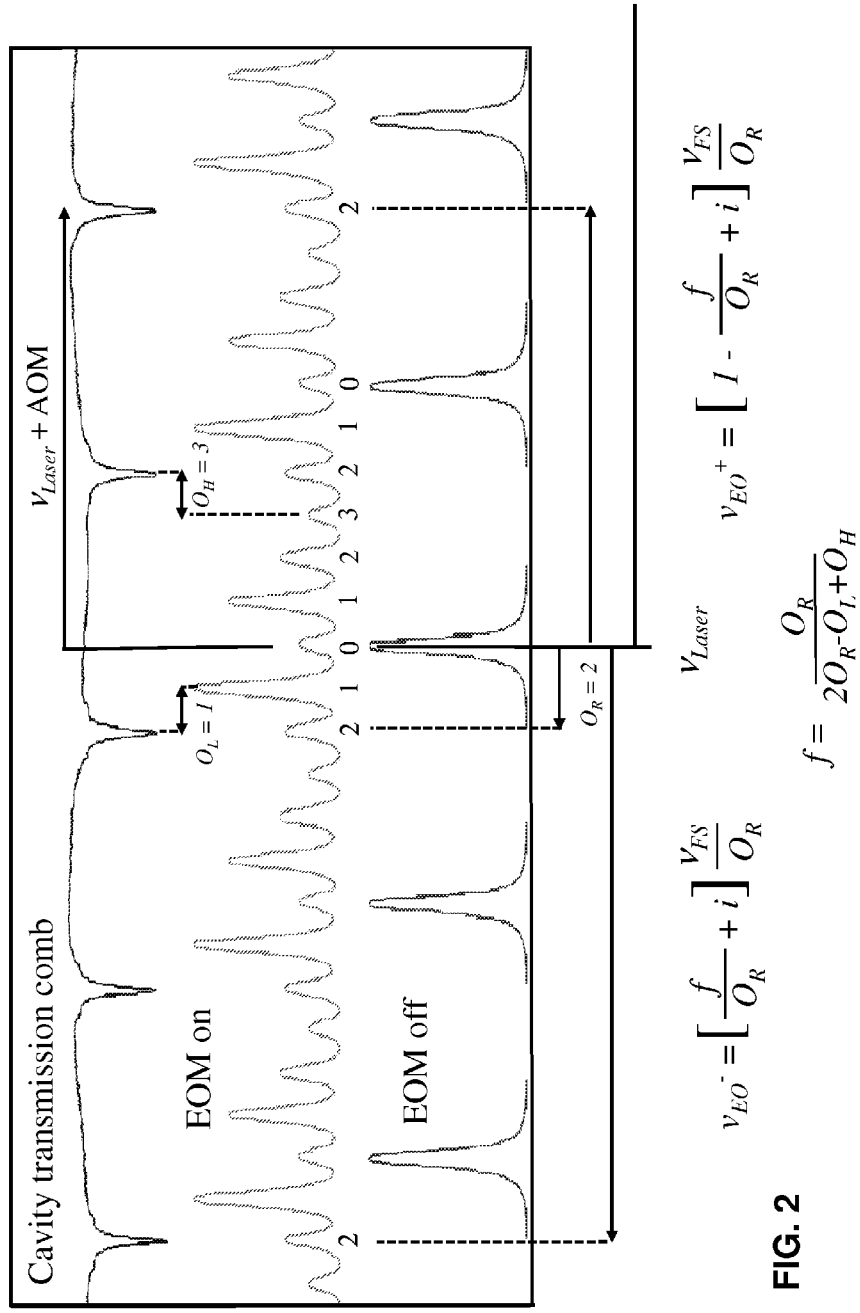
FIG. 2 is a graphical illustration of signals transmitted by the filter cavity as the laser is scanned from lower to higher frequency in accordance with one embodiment of the present disclosure.

Referring now to FIG. 2, shown is a graphical representation of the continuous wave signals reflected or transmitted by the filter cavity (shown at 110 of FIG. 1). The signals may be measured as the laser is scanned in frequency for fixed cavity length. The filter cavity may be a one-half meter (0.5 m) confocal resonator having a mode spacing, $\Delta v_{MS}$, of 150 MHz. The top trace is the reflected cavity signal of the lock leg, with each reflection dip at resonance having the fifteen Megahertz (15 MHz) sidebands used for stabilization purposes appearing as shoulders. The cavity transmission of scan leg is shown as the lower trace with the EOM driving field off. The frequency offset relative to the lock leg is a result of the AOM shift of 250 MHz.

The middle trace is the filter transmission of the scan leg when a 50 MHz continuous wave signal from the AWG is applied to the EOM. Under these conditions, only the negative second-order sideband is resonant while the other second-order, two first-order, two third-order sidebands and diode laser signals are reflected.

Generally, the diode laser offset frequency for transmission of the sideband of order, $O_R$, may be determined according to the following equation:

$$f=O_R/(2O_R-O_L+O_H) \quad \text{(Equation 1)}$$

where $O_L$ and $O_H$ are, respectively, the lowest- and highest-order sidebands to reflect.

In FIG. 2, $O_L=1$ and $O_H=3$ to give $f=\frac{1}{3} \Delta v_{MS}$ or 50 MHz. This formula assumes that power in the $O_H+1$ is negligibly small as this order will be resonant. It is further noted that by subtracting 0.5 from the denominator in Equation 1, the order, $O_H$, for sideband rejection will be doubled at the cost of halving the frequency difference between a cavity resonance and the two lower order sidebands, $O_H$ and $O_H+1$. Further improvements in spectral purity may be realized by tuning the Bessel function power distribution of the EOM response. In lieu of a confocal filter cavity, an I/Q modulator or Mach-Zehnder interferometer may also be used as an alternative method for single sideband selection.

Once f is determined, the AWG (or other tunable microwave source) may be programmed with two series of frequencies separated by desired frequency step, $\Delta v_{FS}$, where $\Delta v_{FS}=n \, \Delta v_{MS}$ (n=1, etc) and $\Delta v_{MS}$ is the minimum mode spacing of the resonator according to the following equations:

$$v_{EO}^+(i)=[f/O_R+i]\Delta v_{FS}/O_R \quad \text{(Equation 2)}$$

$$v_{EO}^-(i)=[1-f/O_R+i]\Delta v_{FS}/O_R \quad \text{(Equation 3)}$$

where $v_{EO}^+(i)$ and $v_{EO}^-(i)$ are the transmitted positive and negative sideband frequency branches, respectively, for microwave frequencies defined for different i up to the high frequency limit of the electro-optic modulator.

Higher finesse cavities may quickly improve the spectral purity for a given laser offset as given by the Airy transmission function. However, for the purpose of rapid scans of an absorbing medium external to the filter cavity, a tradeoff with cavity finesse may be required to achieve fast switching rates. For this reason, a cavity finesse near 44 may be chosen for this application.

Referring now to FIGS. 3A and 3B, shown are graphical illustrations of the measured spectral purity (FIG. 3A) versus switching speed (FIG. 3B). In accordance with these figures, the EOM is driven with 400 nsec long square pulses from the AWG. The measured diode laser transmission in the scan leg, when offset by 50 MHz (f=⅓) using the lock leg is 1.2%, in good agreement with Airy function predictions at this finesse. The measured switching speed following a square pulse response of the EOM is shown in the lower panel. The fitted decay constant is twenty-four nanoseconds (24 nsec) which is in good agreement with the time bandwidth product expected for the seven Megahertz (7 MHz) FWHM width of the transmission peak. These properties indicate that contributions to the time response from the AWG electronics and EOM responses may be comparatively small.

The $V_\pi$ phase shift condition of the EOM may have a frequency dependence that scales by, for example, 1.5 over the range from 1 GHz to 10 GHz. Other standing wave issues (optical or electrical) may also lead to slight variations in the sideband power delivered by the EOM. The digital amplitude control of the waveforms may be convenient for power-leveling purposes. Power-leveling may have advantages for direct absorption detection where the impact of problems with the reference power ratio is minimized.

The leveling of sideband powers using the AWG may be performed in two steps. First, the Bessel function distribution of the transmitted sideband at each frequency step may be determined by delivering a series of linearly increasing microwave voltages and integrating the optical signal powers on the reference detector at each step. Then, across all calibration curves, a reasonable reference power level may be selected and the corresponding lowest interpolated voltage may be determined at each frequency step. These course calibration curves have been found to hold over the full tuning range of the diode laser (1597 nm to 1645 nm). Small corrections to the waveform voltage required at other diode laser frequencies may be performed by again integrating the optical signal powers at each frequency step and adjusting the waveform amplitudes, $A_{MW}(i)$, in a non-linear way according to the following formula:

$$A_{MW}(i)=(I_{damp}+I_{Ave})/(I_{damp}+I_i) \qquad \text{(Equation 4)}$$

where $I_{damp}$ is chosen to be two or three times the average value, $I_{Ave}$, of the integrated amplitudes.

Referring now to FIGS. 4A and 4B, shown are graphical illustrations of the measured absorption signals of a gas mix in dry air over a multi-pass cell and at atmospheric pressure. More particularly, the measured absorption signals are shown of a gas mix of 5400 ppm carbon dioxide $CO_2$ (~×14 ambient level) in dry air over a multi-pass cell path length of 45 meters and at atmospheric pressure. In this particular instance, the absorption path could be used for measuring the direct absorption spectrum in a sample cell. Similarly, it could be used for measuring hard target absorption in the atmosphere.

In FIG. 4A, illustrated are the raw time domain signals measured on the reference detector (top trace) and signal detector (lower trace). These signals are measured with each sideband pulse at a given frequency for one hundred nanoseconds (100 nsec) at a given frequency and then off for 100 nsec for one hundred twenty-three (123) pulses. Each scan may make use of the second order sidebands with a frequency step size of three hundred (300) MHz and covers 37.5 GHz in 25 µs (1,500 THz/sec). In this case, the maximum speed is determined by the minimum amount of time it takes to switch between different frequencies, in this case 200 nsec. The minimum amount of time to cover the 123 frequencies is 25 µs. The measurement technique used here is for a direct absorption spectrum. Alternatively, it is representative of an absorption spectrum over a commensurate path in the atmosphere.

Referring now to FIG. 4A, the top two traces show the integrated signals from reference and signal channels. The power in the reference channel may be flattened. In just one or two iterations, the power flatness is typically better than one percent (1%) across nearly the full tuning range, except for pulses near the highest microwave frequencies that fall below the reference level chosen for normalization. The absorbance spectrum of carbon dioxide ($CO_2$) at 5400 ppm is shown in FIG. 4B. Superimposed onto FIG. 4B is the fit to a Voigt profile, with residual signals shown as the lower trace. The intensity and pressure broadened width are in good agreement with the published values. Referring now to FIG. 4C, illustrated are the measured integrated intensities of methane at the ambient level concentration of 1.8 ppm in room air. The intensities are shown as a function of time where each intensity may be fit to a single 25 µsec scan. Over a period of one second, 40,000 measurements may be performed. From these data, the noise equivalent absorption (NEA) is estimated to be $5\times10^{-9}$ $cm^{-1}$ $Hz^{-1/2}$ for a 45 m path and this sensitivity and speed may be the best that has ever been achieved for a direct absorption method.

For longer term measurements that extend ten (10) minutes or longer, it may be advantageous to provide an absolute frequency reference for the diode laser. This may be achieved by locking the zero order beam from the AOM (with 15 MHz sidebands) to an optical transfer cavity. The transfer cavity may be actively locked to a polarization stabilized helium neon laser ($\Delta v_{RMS}$<0.5 MHz) using a piezoelectric transducer (PZT) and heater. This type of system may have a long term absolute frequency stability of better than ±0.5 MHz.

In one embodiment of the present disclosure, a high finesse optical cavity may be used in order to increase the effective path length of the absorption cell. Referring now to FIG. 5A, such a high finesse optical cavity could be used as the filter cavity. Such a high finesse filter cavity, or any stable resonator, may be used to perform absorption measurements of a gas analyte placed within it. At present, this reflectivity is within a few hundred parts per million (ppm) of unity. Very long path lengths that exceed 1 kilometer (1 km) may be possible.

In the embodiment of FIG. 5A, illustrated is a diagram of a fast switching arbitrary frequency light source in accordance with another embodiment of the present disclosure. Components of the light source 500 include a laser device 505, a filter cavity 510 that provides for single sideband selection, and a waveguide based electro-optic modulator (EOM) 515 that is driven by a tunable microwave source 520. Also illustrated is a photoreceiver used to measure the cavity transmission. The EOM 515 generates sidebands 517. In one application using the embodiment with a high finesse filter cavity having an absorbing medium as shown in FIG. 5A, a sample may be introduced between the mirrors of the cavity 510 and the light source may be switched for a sufficient duration to fill the cavity 510 with light. There may be at least two mirrors 512, 513, each of which is disposed at the end of the filter cavity 510. The light source may then be turned off. The light that leaks out through one of the mirrors is measured as a decay rate. This spectroscopic technique is known as cavity ringdown spectroscopy (CRDS). Once the decay rate is known for the empty cavity, the change in the rate constant when the sample is introduced at known temperature and pressure is directly proportional to the absorption rate constant of the sample.

Referring now to FIG. 5B, illustrated are the cavity resonances $\omega_f$. In FIG. 5C, illustrated are the sidebands 517 generated by the electro-optic modulator 515 of FIG. 5A. As shown in FIGS. 5C and 5D, the circled frequency of the EOM (FIG. 5A; 515) is resonant with filter cavity 510. That is, the single selected sideband of the electro-optic modulator is resonant with optical cavity modes of the filter cavity (FIG. 5A; 510).

Figures 6A, 6B:
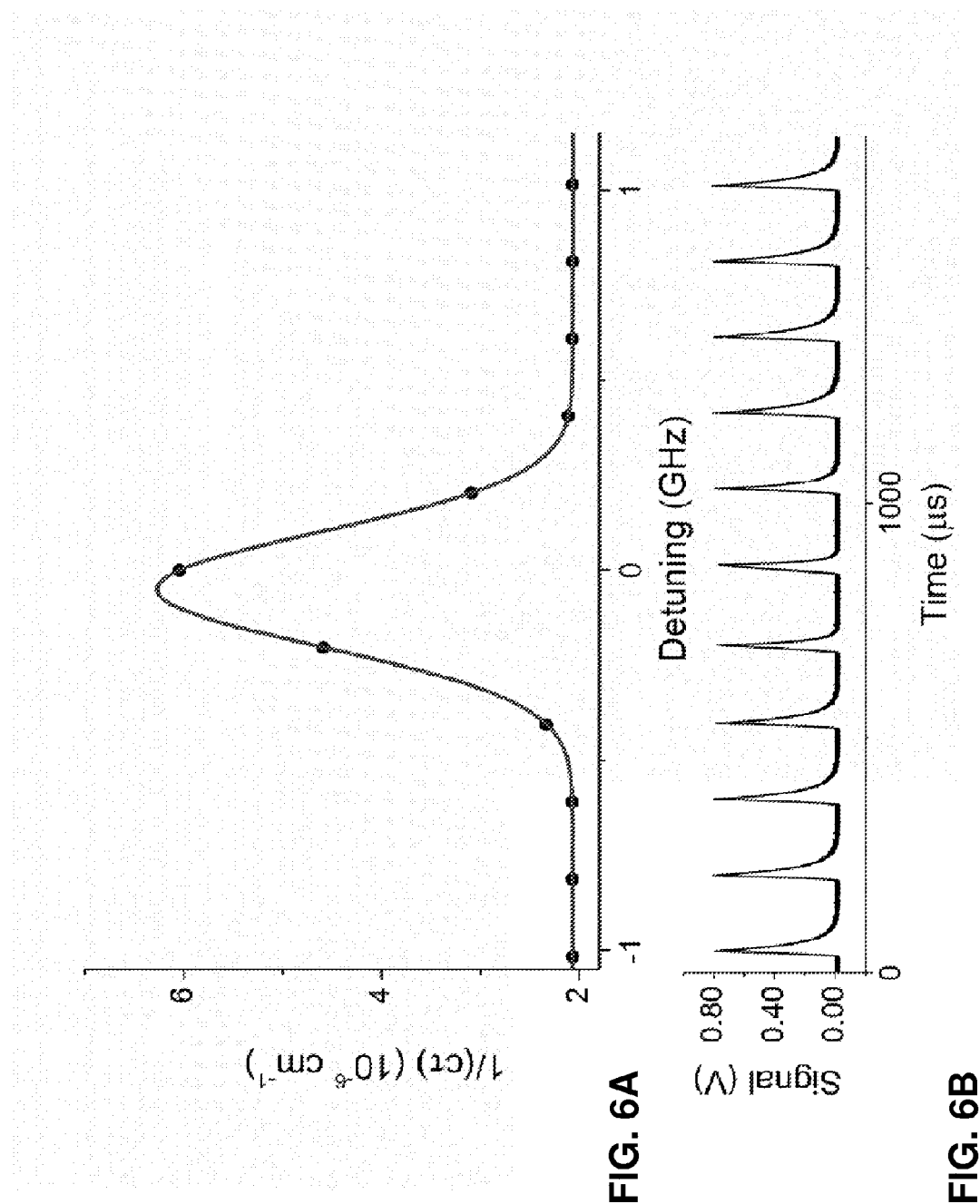
FIGS. 6A and 7 are graphical illustrations of typical measured spectra using cavity-enhanced spectroscopy, particularly cavity ring down spectroscopy, in accordance with one embodiment of the present disclosure.
FIG. 6B is a real-time data acquisition trace which demonstrates that the measurement of FIG. 6A is performed without any dead time.

Referring now to FIG. 6A, illustrated is a typical measured spectrum using CRDS of the (30012)←(00001) P14e $CO_2$ transition for a $CO_2$ sample at a pressure of 12 pascals (Pa). The data were fit to a speed-dependent Nelkin-Ghatak line shape function. In FIG. 6A, the data is shown as dots and the Nelkin-Ghatak line shape function is shown as a solid line. Also shown in FIG. 6B is a real-time data acquisition trace in which 11 ring-down decays are recorded in ~2 milliseconds. Thus, demonstrating that the measurement can be performed at the maximum possible rate. We define maximum measurement technique for CRDS is the time it takes to record a single ring-down event. In this case, the maximum speed is the minimum amount of time it takes to switch between different ring-down decays, in this case 182 µs. The minimum amount of time to cover 11 ring-down frequencies is 2 milliseconds. The measurement technique used here is for cavity-enhanced spectroscopy.

Figure 7:
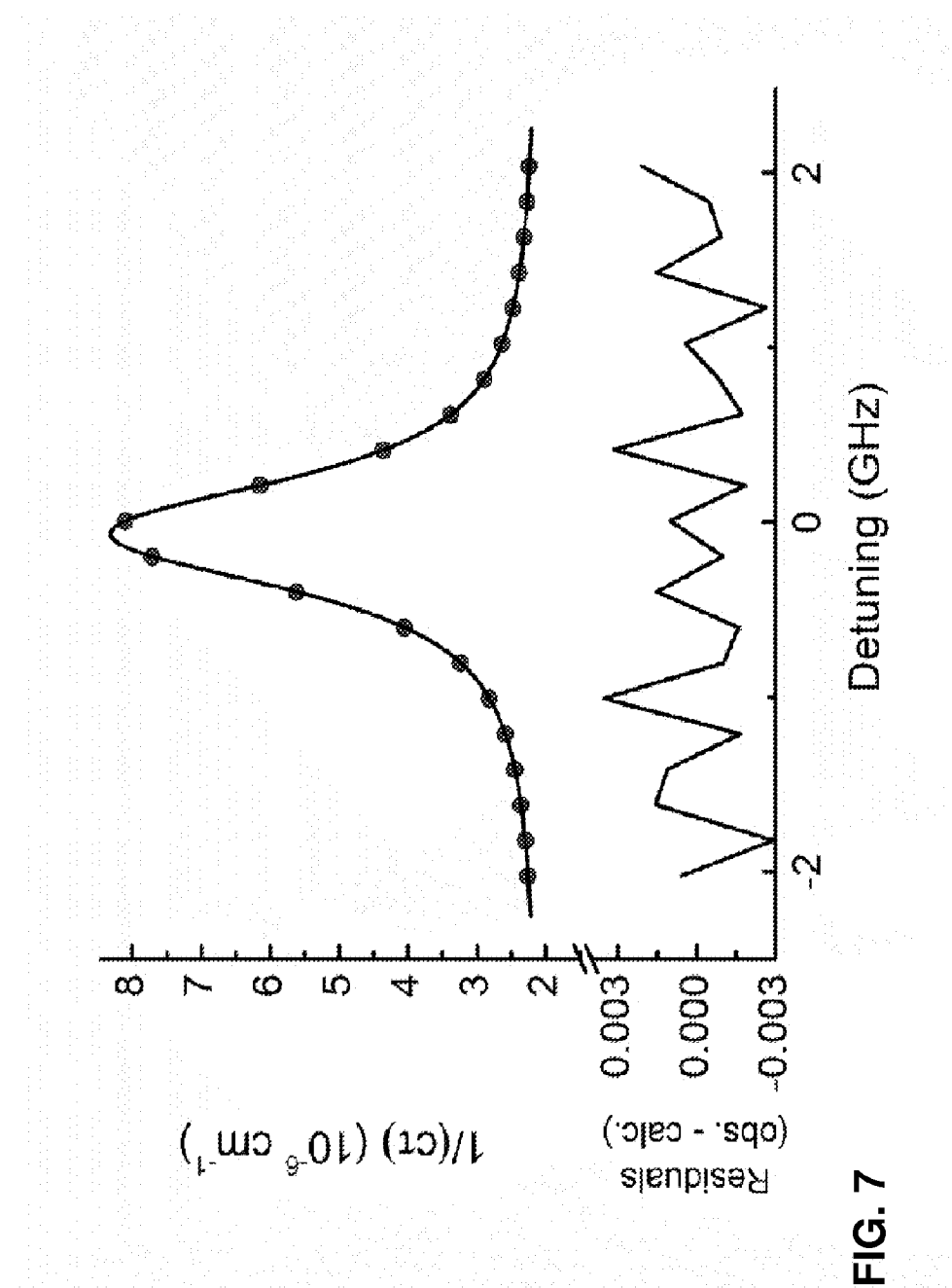

FIG. 7 illustrates another $CO_2$ spectrum with the corresponding residuals found below. In this case, the mirror reflectivity is 99.985% and the effective path length is nearly 5 km. Because of the laser stabilization method described above in connection with FIG. 1, and the high finesse of the cavity, the measured relative line width of the laser is less than 150 Hz. The empty cavity decay rate is 16 us and each independent measurement was performed over time period of ~0.15 ms to give a ~6 kHz scan rate.

Because of the high frequency precision and fast switching speed of the light source of the present disclosure, the scan time to measure 11 points across the full line in FIG. 6A is about two milliseconds (2 ms). The scan time may be more than an order-of-magnitude faster than any other CRDS method. As a result of using this EOM scan based method, the relative standard deviation in the time constants is 0.008% and yields a noise-equivalent-absorption of $1.7 \times 10^{-12}$ $cm^{-1}$ $Hz^{-1/2}$.

The CRDS technique described herein may have significant advantages over other cavity-enhanced spectroscopic methods. It offers a high scanning speed. The scan is performed in the shortest possible time and therefore, at the maximum possible rate, limited by the speed of light. This CRDS technique also offers a wide scanning range and high frequency fidelity. In addition, the use of an EOM to initiate the ring-down decays leads to a high extinction and thus, lower noise on the ring-down decays. This method is widely applicable to many trace gas sensing applications. In comparison with other broadband CRDS methods, this sensitivity and speed may be the best that has ever been achieved.

While the specification describes particular embodiments of the present invention, those of ordinary skill can devise variations of the present invention without departing from the inventive concept.

We claim:

1. A fast switching arbitrary frequency light source for broadband spectroscopic applications, the light source comprising:
a waveguide-based electro-optic modulator;
a tunable microwave source configured to drive the electro-optic modulator, wherein the tunable microwave source has a speed substantially commensurate with, or exceeding, the slower of a measurement speed of the waveguide-based electro-optic modulator or a maximum speed of a spectroscopic measurement technique;
a selection device configured to select a single frequency component from multiple discrete frequencies of the electro-optic modulator; and
a laser device configured to stabilize the laser device to the selection device.

2. The light source of claim 1, further comprising:
a splitting device configured to stabilize the laser device relative to the selection device.

3. The light source of claim 2, wherein the splitting device is configured to sample the output of the laser device prior to the selection device, and to split the output from the laser device into a lock leg and a scan leg; and
wherein the split output to the lock leg is at a level sufficient to detect reflected power from the cavity and to stabilize the laser relative to the selection device; and
wherein the scan leg is configured to add at least one tunable sideband, only one of which sidebands is resonant with a filter cavity mode.

4. The light source of claim 1, further comprising:
a detection sensitivity improvement device configured to improve detection sensitivity by increasing the total optical path length through a sample volume.

5. The light source of claim 4, further comprising:
a measuring device configured to measure an absorption signal of an absorbing medium and reference power of the laser device at each step of the tunable microwave source.

6. The light source of claim 1, wherein the tunable microwave source is an arbitrary waveform generator.

7. The light source of claim 1, wherein the selection device is an optical interferometer.

8. The light source of claim 7 wherein the optical interferometer is an optical resonator defined by at least two mirrors, the optical interferometer being selected from the group consisting of a Fabry-Perot confocal filter cavity, an IQ modulator and a Mach Zehnder interferometer.

9. The light source of claim 1, wherein the selection device is an optical cavity defined by at least two mirrors, the selection device having an absorbing medium in an optical path between the at least two mirrors, and the light source further comprises:
a cavity enhancement device configured to select a single sideband of the electro-optic modulator, said sideband being resonant with optical cavity modes of the cavity enhancement device.

10. A fast switching arbitrary frequency light source for broadband spectroscopic applications involving cavity enhanced measurements, the light source comprising:
a waveguide-based electro-optic modulator;
a tunable microwave source configured to drive the electro-optic modulator, wherein the tunable microwave source has a tuning speed substantially commensurate with the slower of a tuning speed of the waveguide-based electro-optic modulator or a maximum scan speed of the spectroscopic measurement technique;
a filter cavity defined by at least two mirrors, the filter cavity being configured to select a single frequency component from multiple discrete frequencies of the electro-optic modulator, wherein the filter cavity further includes an absorbing medium in an optical path between the at least two mirrors;
a laser device configured to stabilize the laser device relative to the filter cavity;

a beam splitter configured to sample at least a portion of the output from the laser device and to use that sampled portion to stabilize the laser device relative to the filter cavity;

a detection sensitivity improvement device configured to improve detection sensitivity by increasing the total optical path length through a sample volume; and a cavity enhancement device configured to allow the stepping of the laser sideband into resonance with optical cavity modes of the cavity enhancement device.

11. The light source of claim 10, wherein the beam splitter is configured to sample the output of the laser device prior to the filter cavity, and to split the output from the laser device into a lock leg and a scan leg; and wherein the split output to the lock leg is at a level sufficient to detect reflected power from the cavity and to stabilize the laser relative to the selection device; and wherein the scan leg is configured to add at least one tunable sideband, only one of which at least one sideband is resonant with a filter cavity mode.

12. The light source of claim 11, further comprising:
a laser servo loop configured to stabilize the frequency of the laser device relative to the filter cavity.

13. The light source of claim 12, wherein the laser servo loop includes:
a Pound-Drever-Hall lock device configured to lock the laser device relative to the filter cavity in order to obtain a maximum throughput from the scan leg through the filter cavity.

14. A method for providing a fast switching arbitrary frequency light source, the method comprising:
providing a waveguide-based electro-optic modulator, a tunable microwave source, a laser device and a selection device;
driving the electro-optic modulator with the tunable microwave source;
selecting a single frequency component from multiple-discrete frequencies received from the electro-optic modulator; and
stabilizing the laser device relative to the selection device, including by providing a frequency offset that stabilizes the laser device relative to the selection device.

15. The method of claim 14, wherein the selection device is a filter cavity having an absorbing medium disposed between at least two mirrors.

16. The method of claim 15, further comprising:
receiving the output from the laser device, and splitting the output from the laser device into a lock leg and a scan leg, wherein the output to the lock leg is at a level sufficient to detect reflected power from the filter cavity and to further stabilize the laser device relative to the filter cavity; and
adding at least one tunable sideband, only one of which at least one sideband is resonant with the filter cavity.

17. The method of claim 16, wherein the stabilizing step further includes providing a Pound-Drever-Hall lock device configured to stabilize the laser device relative to the selection device.

18. The method of claim 14, further comprising:
improving detection sensitivity, including by increasing the total optical path length through a sample volume.

19. The method of claim 18, further comprising:
measuring an absorption signal of an absorbing medium and reference power of laser device at each step of the tunable microwave source.

20. The method of claim 15, further comprising:
measuring cavity ring-down signals of a sample between the mirrors of the filter cavity over a path length determined by the filter cavity.

21. The method of claim 14, further comprising:
measuring a hard target absorption spectrum of a sample.

22. The method of claim 14, wherein the tunable microwave source is an arbitrary waveform generator.

23. The method of claim 14, wherein the selection device is selected from the group consisting of a Fabry-Perot confocal filter cavity, an IQ modulator and a Mach Zehnder interferometer.

24. The method of claim 14, wherein the selection device is an optical cavity defined by at least two mirrors, the selection device having an absorbing medium in an optical path between the at least two mirrors, and the method further comprises:
stepping a selected laser sideband between successive optical cavity modes of the filter cavity.

* * * * *